(12) United States Patent
Sevenster et al.

(10) Patent No.: US 11,775,585 B2
(45) Date of Patent: Oct. 3, 2023

(54) SYSTEM AND METHOD FOR PRIORITIZATION AND PRESENTATION OF HETEROGENEOUS MEDICAL DATA

(71) Applicant: KONINKLIJKE PHILIPS N.V., Eindhoven (NL)

(72) Inventors: Merlijn Sevenster, Haarlem (NL); Eran Rubens, Palo Alto, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/056,161

(22) PCT Filed: May 1, 2019

(86) PCT No.: PCT/EP2019/061166
§ 371 (c)(1),
(2) Date: Nov. 17, 2020

(87) PCT Pub. No.: WO2019/219388
PCT Pub. Date: Nov. 21, 2019

(65) Prior Publication Data
US 2021/0279289 A1   Sep. 9, 2021

Related U.S. Application Data

(60) Provisional application No. 62/673,155, filed on May 18, 2018.

(51) Int. Cl.
*G06F 16/903* (2019.01)
*G16H 10/60* (2018.01)
(Continued)

(52) U.S. Cl.
CPC .... *G06F 16/90335* (2019.01); *G06F 16/9035* (2019.01); *G06F 16/90332* (2019.01); *G06F 40/242* (2020.01); *G16H 10/60* (2018.01)

(58) Field of Classification Search
CPC ......... G06F 16/90335; G06F 16/90332; G06F 16/9035; G06H 10/60
See application file for complete search history.

(56) References Cited

U.S. PATENT DOCUMENTS 9,348,813 B2 * 5/2016 Mankovich ............. G06F 40/30
2010/0106522 A1   4/2010 Cooper
(Continued)

FOREIGN PATENT DOCUMENTS

WO   2013036677        3/2013
WO   WO2013036677 A1 *  3/2013
(Continued)

OTHER PUBLICATIONS

Collaborative Denoising Auto-Encoders for Top-N Recommender Systems; Wu et al. ACM 2015.*
(Continued)

*Primary Examiner* — Daniel A Kuddus

(57) ABSTRACT

A system and method prioritizes and presents heterogenous medical data. The method includes retrieving medical data of a patient, the medical data including data from multiple data sources. The method includes phenotyping the medical data to generate a reasoning trail and reasoning outcome including one or more codes, the reasoning trail including a basis for which the reasoning outcome is determined. The method includes assigning a relevance score to each of the one or more codes. The method includes ranking the codes based on the relevance score of each of the one or more codes. The method includes displaying the codes in rank order.

21 Claims, 4 Drawing Sheets

(51) Int. Cl.
*G06F 16/9032* (2019.01)
*G06F 16/9035* (2019.01)
*G06F 40/242* (2020.01)

(56) References Cited

U.S. PATENT DOCUMENTS

| | | | | |
|---|---|---|---|---|
| 2011/0046979 A1* | 2/2011 | Tulipano | ............... | G16H 50/20 |
| | | | | 707/E17.014 |
| 2012/0035963 A1* | 2/2012 | Qian | ............... | G16H 30/20 |
| | | | | 705/3 |
| 2014/0067847 A1* | 3/2014 | Barbieri | ............... | G16H 50/70 |
| | | | | 707/765 |
| 2014/0108047 A1* | 4/2014 | Kinney | ............... | G16H 10/60 |
| | | | | 705/3 |
| 2014/0149407 A1* | 5/2014 | Qian | ............... | G06F 16/35 |
| | | | | 707/758 |
| 2014/0343925 A1* | 11/2014 | Mankovich | ............... | G06F 40/169 |
| | | | | 704/9 |
| 2015/0149215 A1* | 5/2015 | Qian | ............... | G06F 16/335 |
| | | | | 705/3 |
| 2015/0161329 A1* | 6/2015 | Mabotuwana | ............... | G16H 10/60 |
| | | | | 705/3 |
| 2016/0019299 A1 | 1/2016 | Boloor | | |
| 2016/0078188 A1 | 3/2016 | Ashparie | | |
| 2017/0235892 A1* | 8/2017 | Sevenster | ............... | G16H 30/20 |
| | | | | 705/2 |
| 2017/0351806 A1* | 12/2017 | Beim | ............... | G16B 20/20 |
| 2018/0121604 A1 | 5/2018 | Naeymi-Rad | | |

FOREIGN PATENT DOCUMENTS

| | | | |
|---|---|---|---|
| WO | WO2013036677 A1 * | 3/2013 | |
| WO | 2017/172629 | 10/2017 | |
| WO | 2017167704 | 10/2017 | |
| WO | 2017202631 | 11/2017 | |

OTHER PUBLICATIONS

International Search Report and Written Opinion dated Jul. 9, 2019 for International Application No. PCT/EP2019/061166 Filed May 1, 2019.

Lasko, et al: "Computational Phenotype Discovery Using Unsupervised Feature Learning over Noisy, Sparse, and Irregular Clinical Data", PLOS ONE, Jun. 2013, vol. 8, Issue 6.

* cited by examiner

| Original data source | Meaningful fragment from the original data source | Supportive evidence within the meaningful fragment | Reasoning dialogue | Reasoning outcome |
|---|---|---|---|---|
| Radiology report | Paragraph of text | A noun phrase that is mapped onto a certain ontology code (e.g., diabetes) | A statement conveying "based on interpretation of the radiology report, patient suggestive of diabetes" | True - patient is suspected to be diabetic |
| Lab values | One lab measurement (e.g., A1c = 7.8%) | Most recent A1c score >= 7% | A statement conveying "based on interpretation of the latest available A1C value, patient suggestive of diabetes" | True - patient is suspected to be diabetic |
| Problem list | A code on the problem list | The code appearing in a controlled list of diabetes-related codes | "Based on interpretation of the patient problem list, patient suggestive of diabetes" | True - patient is suspected to be diabetic |

FIG. 3

SYSTEM AND METHOD FOR PRIORITIZATION AND PRESENTATION OF HETEROGENEOUS MEDICAL DATA

CROSS REFERENCE TO RELATED APPLICATIONS

This application is the U.S. National Phase application under 35 U.S.C. § 371 of International Application No. PCT/EP2019/061166 filed May 1, 2019, which claims the benefit of U.S. Provisional Patent Application No. 62/673,155 filed May 18, 2018. These applications are hereby incorporated by reference herein.

BACKGROUND

A patient's Electronic Medical Record (EMR) may include a wide variety of clinical data sources such as, for example, problem lists, lab values, medication lists and free-text documents including admissions and discharge notes along with pathology, radiology and operation reports. The available data from the various data sources may be displayed on a graphical user interface (GUI). The amount of clinical data recorded for a patient, however, supersedes the processing power of medical workers. The large volume of data presented to a user (e.g., physician, nurse, medical technician, etc.) via the GUI results in a time-consuming and inefficient review process. In addition, due to the large volume of available data, information from the various data sources are often displayed with the most recently acquired and/or recently available data appearing first. Consequently, the user may only review the patient data that has become recently available and/or consult selected data sources within the patient's medical chart, potentially missing relevant information. For example, medical workers may only check the latest lab values, potentially missing relevant medications or outcomes of pathology reports.

SUMMARY

The exemplary embodiments are directed to a method, comprising: retrieving medical data of a patient, the medical data including data from multiple data sources; phenotyping the medical data to generate a reasoning trail and reasoning outcome including one or more codes, the reasoning trail including a basis for which the reasoning outcome is determined; assigning a relevance score to each of the one or more codes; ranking the codes based on the relevance score of each of the one or more codes; and displaying the codes in rank order.

The exemplary embodiments are directed to a system, comprising: a non-transitory computer readable storage medium storing an executable program; and a processor executing the executable program to cause the processor to: retrieve medical data of a patient, the medical data including data from multiple data sources; phenotype the medical data to generate a reasoning trail and reasoning outcome including one or more codes, the reasoning trail including a basis for which the reasoning outcome is determined; assign a relevance score to each of the one or more codes; rank the codes based on the relevance score of each of the one or more codes; and display the codes in rank order.

The exemplary embodiments are directed to a non-transitory computer-readable storage medium including a set of instructions executable by a processor, the set of instructions, when executed by the processor, causing the processor to perform operations, comprising: retrieving medical data of a patient, the medical data including data from multiple data sources; phenotyping the medical data to generate a reasoning trail and reasoning outcome including one or more codes, the reasoning trail including a basis for which the reasoning outcome is determined; assigning a relevance score to each of the one or more codes; ranking the codes based on the relevance score of each of the one or more codes; and displaying the codes in rank order.

BRIEF DESCRIPTION OF THE DRAWINGS

FIG. 3 shows a table illustrating an exemplary reasoning trail provided by an exemplary phenotyping engine of the system of FIG. 1.

DETAILED DESCRIPTION

Figure 1:
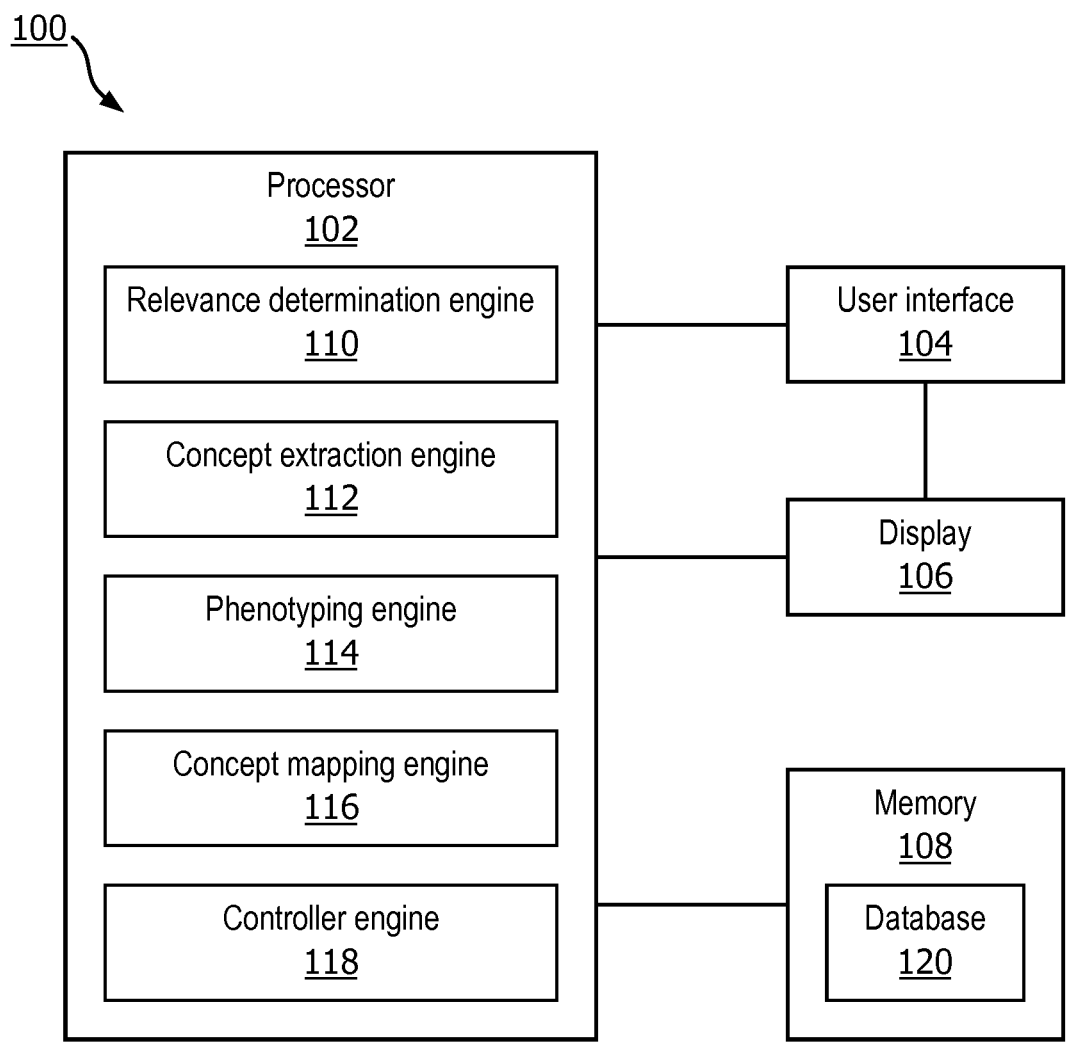
FIG. 1 shows a schematic drawing of a system according to an exemplary embodiment.

The exemplary embodiments may be further understood with reference to the following description and the appended drawings, wherein like elements are referred to with the same reference numerals. The exemplary embodiments relate to systems and methods for prioritizing information from heterogeneous medical data sources and presenting the relevant information to a user in the context of the user's workflow setting. The relevant clinical data may be presented to the user via a user interface which improves navigability between the various data sources and ensures review of all relevant information so that the user may provide more accurate diagnoses and/or analyses and superior patient treatment. It will be understood by those of skill in the art that users may include any type of medical professional, including, for example, doctors, nurses, medical technicians, etc. It will also be understood by those of skill in the art that the exemplary embodiments may be utilized to prioritize information from any of a variety of clinical data sources in any of a variety of hospital settings.

As shown in FIG. 1, a system 100, according to an exemplary embodiment of the present disclosure, prioritizes information from a variety of data sources, presenting the most relevant information to the user in the context of the user's workflow setting. The system 100 comprises a processor 102, a user interface 104, a display 106, and a memory 108. The memory 108 includes a database 120, which stores patients' medical records. The medical records may include clinical data from a variety of sources such as, for example, medical images (e.g., MRI, CT, CR ultrasound), problem lists, lab values, medication lists, and documents including admissions and discharge notes and pathology, radiology and operation reports.

The processor 102 may include a relevance determination engine 110 for assigning a relevance score to a medical code, a concept extraction engine 112 for extracting concepts from free-text medical documents (e.g., radiology and pathology reports), a phenotyping engine 114 for applying clinical reasoning to determine whether a patient has a particular disease or condition, a concept mapping engine 116 for mapping the extracted phenotypic information onto a medical vocabulary, and a controller engine 118 for retrieving relevant medical data and applying the appropriate engines for prioritizing the relevant medical data. Those skilled in the art will understand that the engines 110-118 may be implemented by the processor 102 as, for example, lines of code that are executed by the processor 102, as firmware executed by the processor 102, as a function of the processor 102 being an application specific integrated circuit (ASIC), etc.

By making selections on the user interface 104, the user, which may include medical workers, including for example, doctors, nurses, medical technicians, etc., may initiate the prioritization and relevance ranking process and/or make selections to review/view data from a prioritized list presented to the user on the display 106. The user may also edit and/or set parameters for the engines 110-118 described above via the user interface 104, which may include, for example, an EMR interface.

Figure 2:
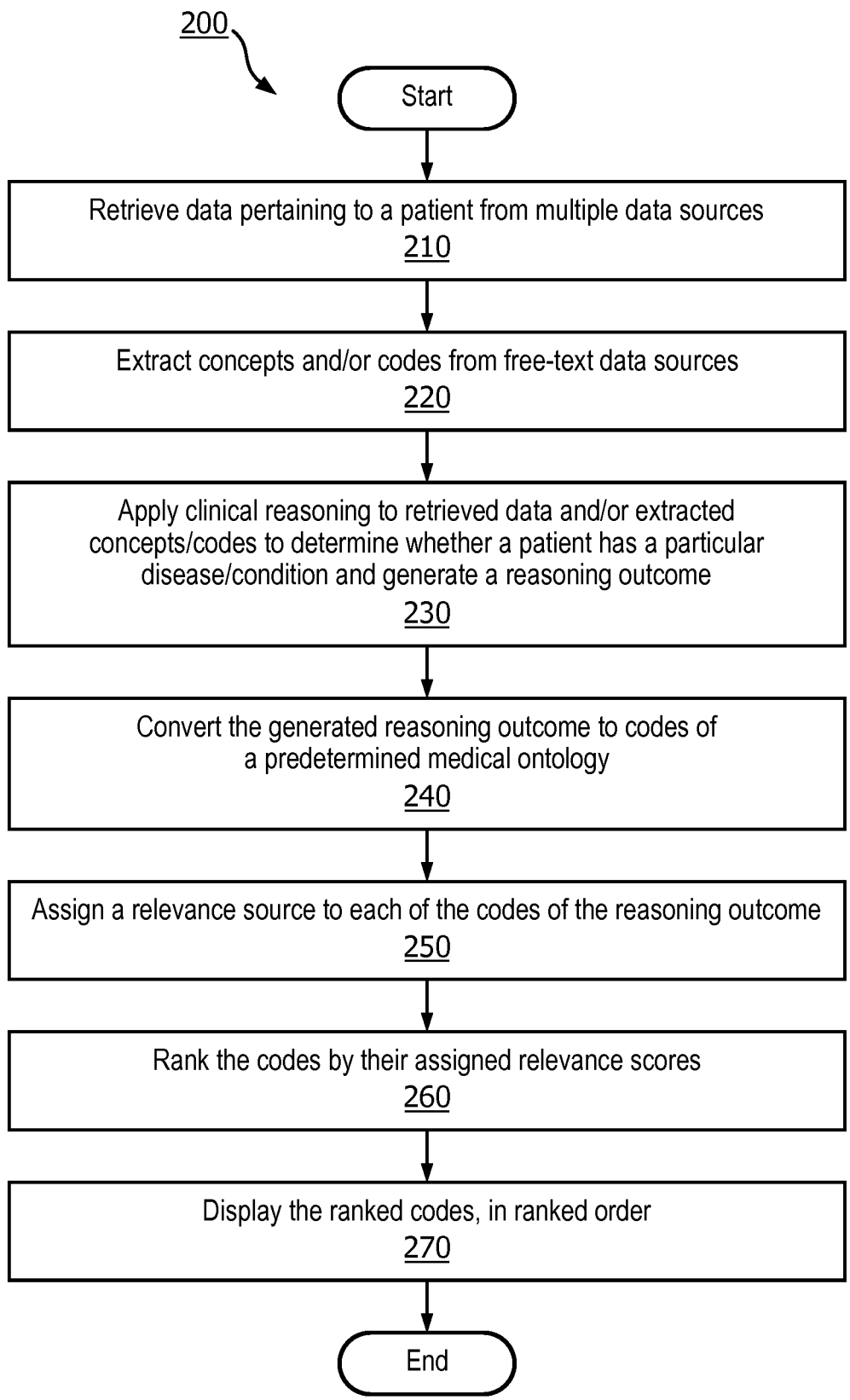
FIG. 2 shows a flow diagram of a method according to an exemplary embodiment.

FIG. 2 shows an exemplary method 200 for prioritizing information from heterogenous medical data sources and presenting information relevant to the user in the context of the user's workflow setting, using the system 100 described above. The method 200 may be executed by the controller engine 118, when initiated or triggered via an event or a user, as will be described in further detail below.

In 210, medical data pertaining to a patient is retrieved from the database 120 using, for example, a database call. The data retrieval may be responsive to a contextual trigger. For example, within a radiology department, an acquisition of an image (e.g., MRI, CT, CR, ultrasound), which must be read or reviewed by the user, may trigger the retrieval of data so that the user may, based on other relevant information, make an informed analysis of the image. In another example, within the oncology department, the user may initiate the retrieval when conducting a patient consult. In yet another example, within the cardiology department, a user may initiate the retrieval when conducting patient preparation for a procedure. It will be understood by those of skill in the art that the retrieval of data from the patient record may be initiated in response to any of a variety of contextual triggers which may be selected and/or input via the user interface.

In 220, free-text medical data sources such as, for example, radiology reports, pathology reports and operation reports, that are retrieved during 210 are transmitted to the concept extraction engine 112. The concept extraction engine 112 processes natural language and applies techniques for extracting ontology concepts from the natural language. In one exemplary embodiment, the concept extraction engine 112 may have knowledge of how a standard document is configured. For example, a radiology report may include specific sections such as TECHNIQUE, CLINICAL HISTORY, COMPARISON, FINDINGS, and CONCLUSIONS. In some cases, the FINDINGS portion being sub-sectioned via anatomical structure. Similarly, the concept extraction engine 112 may have access to knowledge of how other free-text documents such as pathology reports and operation notes are structured so that concept extraction engine 112 may be configured to extract concepts from particular sections of a report being reviewed.

The concept extraction engine 112 may apply sentence boundary detection and/or a phrase detection algorithm to break the text up into sentences or phrases that may be classified according to a part-of-speech algorithm. In one exemplary embodiment, elements from the natural language (e.g., phrase) are matched against concepts from a medical vocabulary to generate a list of medical codes. Medical concepts may, for example, include codes from accepted medical ontology such as, for example, SNOMED (Systematic Nomenclature of Medicine) or ICD (International Classification of Diseases). Relations may be drawn between extracted concepts that are related to one another, with each relation having a standardized semantic interpretation such as, for example, concept X is_site_of concept Y, where X is an anatomical concept. In a particular embodiment, for each extracted concept, it is determined whether it is negated in the context in which it appears or if it is subject to a certainty modifier.

In 230, the phenotyping engine 114 applies clinical reasoning to the concepts extracted in 220 and other data retrieved during 210 to determine if a patient has a certain disease or condition. The outcome of the phenotyping engine may be encoded as one or more concepts or codes. In one exemplary embodiment, the phenotyping engine 114 may run a different module for each detectable condition or disease. Each module, for example, may be a rule accessing one or more EMR data sources to determine whether the patient has a particular condition or disease. In another example, the module may be a complex reasoning mechanism based on machine learning or statistical modelling. For example, a phenotyping rule for diabetes may consult data sources, as follows:

(a) Does the problem list contain a code for diabetes?
(b) Do the lab values contain an A1c value exceeding 7%
(c) Does the medication list contain an insulin medication? The rule can return TRUE, indicating the patient is diabetic, if supportive evidence is found in any of the above data sources. It will be understood by those of skill in the art that this phenotype rule is exemplary only and that more complex Boolean combinations or weighted reasoning along with other data sources may be applied.

The phenotyping engine 114 may provide a reasoning trail, as shown in the table of FIG. 3. The reasoning trail may include information such as, for example, the original data source, meaningful fragments from the original data source(s), supportive evidence within the meaningful fragments, the reasoning dialogue (e.g., a statement specifying the supportive evidence and how it is used in the reasoning process), and the reasoning outcome. Although the reasoning trail illustrated in FIG. 3 a simple rule-based reasoning for determining whether a patient is diabetic, as noted above, it will be understood by those of skill in the art that the supportive evidence, reasoning dialogue and the reasoning outcome may be based on more than one data source when using, for example, a Boolean combination reasoning, weighted evidence, or more complex decision methods created using, for example, machine learning techniques. Although the exemplary embodiment specifically shows and describes a specific phenotyping module for determining whether the patient has diabetes, it will be understood by those of skill in the art that the phenotyping engine 114 may include any number of phenotyping modules, each of which determines whether the patient has a specific condition or disease.

As noted above, the reasoning outcomes of the phenotyping engine may be encoded according to more than one concept or code. Where one or more of the concepts/codes generated by the phenotyping engine are not consistent with the vocabulary or ontology utilized by the relevance determination engine 110, the concept mapping engine 116 maps the concepts/codes from one ontology to another, in 240. For example, the concept mapping engine 116 may include mapping tables mapping SNOMED onto ICD. If, however, all of the concepts/codes are in the same ontology, the method 200 may proceed from 230 directly to 250.

In 250, the relevance of each of the concepts/codes generated by the phenotyping engine 114 and/or mapped via the concept mapping engine 116 is determined via the relevance determination engine 110. The relevance determination engine 110 assigns a relevance score for each of the concepts/codes extracted above. Relevance scores may be mapped via a mapping table. In one embodiment, the relevance determination engine 110 may be context-specific. For example, the relevance determination engine 110 may include a separate table for each recognized context. In the radiology domain, for example, relevant contexts are determined by the section in which the radiological exam is interpreted—e.g., abdomen, neuro, thoracic, etc. Relevant contexts may also be determined by more granular sections of the radiological exam defined via section-modality combinations such as, for example, abdomen-CT and neuro-MR. The context may be determined by the controller engine 118.

In one exemplary embodiment, the relevance score of codes may be conditionally dependent on the presence of other codes. For example, if the patient is a known diabetic, the presence or absence of infection is more salient than in non-diabetics. In this embodiment, a weighing factor $W_{C,D}$ may be applied to adjust the relevance score of a code C, where the codes in D are known to apply to a patient's disease state, D being a set of codes. Thus, in a given context (e.g., abdomen-CT), if code C would have a relevance of R, the adjusted relevance score in the same context may be $R \times W_{C,D}$. The weighing factor $W_{C,D}$ may be based on a lookup table in which every relevant combination of C and D is listed. If E is the set of known codes for a patient, the lookup table is searched for the entry D that is the largest subset of E from among all the entries in the lookup table. For situations in which there are multiple entries for D, there may be a rule in place. For example, the entry D having the highest adjustment weight $W_{C,D}$ may be selected. If a combination is unknown, however, a default adjustment weight of, for example, 1 may be applied—i.e., no adjustment.

To limit the size of the lookup table and to prevent the relevance determination engine 110 from becoming computationally intractable, the size of set D may be limited to, for example, 1, so that the lookup table may have a maximum size of $N^2$, where N is the number of codes in the background ontology. In another embodiment, the sets D of known codes may be "closed under ancestors". In other words, all ancestor codes of codes in D are added to it before searching the lookup table for adjustment weights. For example, if code E11.21 ("Type 2 diabetes mellitus with diabetic nephropathy") is in D, then the codes E11.2 ("Type 2 diabetes mellitus with kidney complications") and E11 ("Type 2 diabetes mellitus") are added. Although the size of the sets D grows as a consequence of the closure operation, the adjustment weights can be specified on a higher level—e.g., all diabetes type 2 codes under E11 as one entry—which may result in shorter and easier to manage look up tables. In yet another embodiment, the adjustment weight may be dependent not only on the set of known codes D, but also on the context of consumption (e.g., abdomen-CT). It will be understood by those of skill in the art that this embodiment will result in more unique combinations of codes, and longer lookup tables. For all of the embodiments, however, lookup tables of the relevance determination engine 110 may be manually configured and edited.

In 260, the controller engine 118 ranks the codes by the relevance scores determined in 250. In 270, the ranked codes are displayed on the display 106, in rank order. The display 106 may display a prioritized list of codes by filtering out those codes that are not sufficiently relevant using a predetermined threshold value of relevance. Displayed codes may be color-coded by relevance and/or via source (e.g., labs, problem list, etc.). Alternatively, or in addition, the display 106 may only show a pre-determined number of codes. The user interface 104, however, may include an option which may be selected to display more codes—e.g., a set of the next most relevant codes.

Based on the ranked and/or prioritized list shown on the display 106, the user may select particular codes to view the original data source(s) from which the codes were extracted. Selecting the codes may also display the reasoning trail, which generated the code. The user may also filter the displayed codes, as desired. For example, the user may filter the codes to show codes from only some selected sources.

Figure 4:
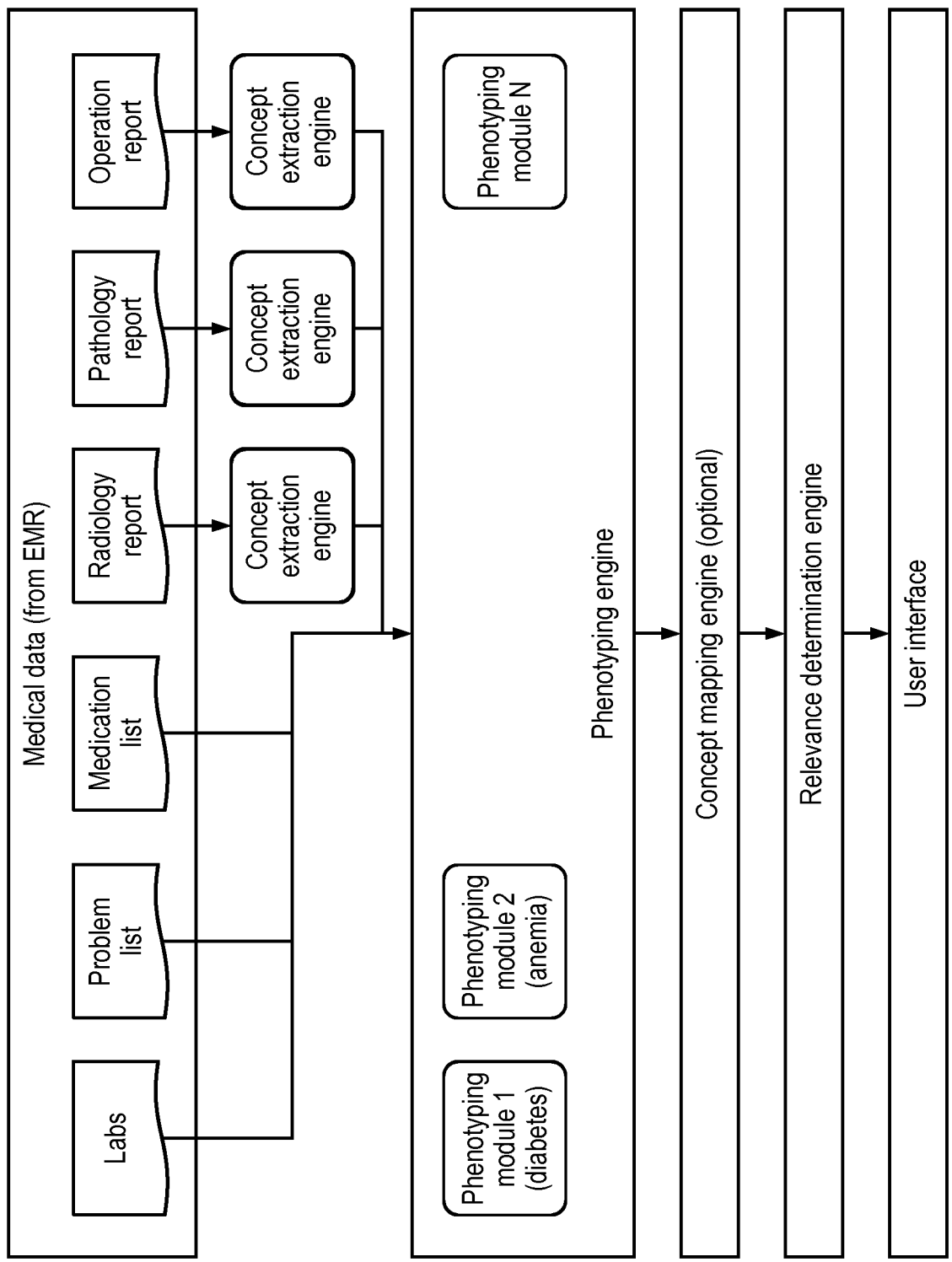
FIG. 4 shows a diagram illustrating a data flow for a system and/or method according to an exemplary embodiment.

FIG. 4 shows a diagram of a data flow according to an exemplary embodiment of the present disclosure. As described above with respect to the method 200, EMR data from heterogeneous sources are transmitted to the phenotyping engine 114 to generate a reasoning trail and outcome. The data transmitted to the phenotyping engine 114 may include concepts extracted from free-text documents via the concept extraction engine 112. Upon extracting concepts/codes via the phenotyping engine 114, data may be optionally transmitted to the concept mapping engine for converting concepts/codes from one medical ontology to another medical ontology that is utilized by the relevance determination engine 110. The relevance determination engine 110 then assigns a (context-specific) relevance score to each of the codes so that a ranked and/or prioritized list of codes may displayed to the user on the display 106 via the user interface 104.

Those skilled in the art will understand that the above-described exemplary embodiments may be implemented in any number of manners, including, as a separate software module, as a combination of hardware and software, etc. For example, the relevance determination engine 110, the concept extraction engine 112, the phenotyping engine 114, the concept mapping engine 116, and the controller engine 118 may be programs containing lines of code that, when compiled, may be executed on the processor 102.

It will be apparent to those skilled in the art that various modifications may be made to the disclosed exemplary embodiments and methods and alternatives without departing from the spirit or scope of the disclosure. Thus, it is intended that the present disclosure cover the modifications and variations provided that they come within the scope of the appended claims and their equivalents.

What is claimed is:

1. A method, comprising:
  retrieving by a controller engine of a processor medical data of a patient, the medical data including data from multiple data sources;
  extracting by a concept extraction engine of the processor ontology and medical concepts from the medical data of the patient including free-text documents by processing natural language;
  phenotyping, using a machine learning model, by a phenotyping engine of the processor the medical data of the patient and the ontology and medical concepts to generate a reasoning trail and reasoning outcome including one or more medical codes and concepts and converting the one or more medical codes and concepts to a predetermined medical ontology, the reasoning trail including a basis for which the reasoning outcome is determined;
  mapping by a concept mapping engine of the processor medical codes and concepts onto a medical vocabulary or ontology from one ontology to another and proceeding to the following assigning step; or when all of the one or more concepts and medical codes are in the same ontology proceeding directly to the following assigning step;

assigning by a relevance determination engine of the processor a relevance score to each of the one or more medical codes and concepts;

ranking by the controller engine the medical codes and concepts based on the relevance score of each of the one or more medical codes and concepts;

color coding at least one of the ranked medical codes or concepts; and displaying the color coded medical codes and concepts in rank order.

2. The method of claim 1, wherein a subset of the relevance scores of the medical codes are conditionally dependent on the presence of other medical codes and concepts, and wherein the method further comprises:

filtering the ranked medical codes wherein only the medical codes having a relevance score above a predetermined threshold value are displayed.

3. The method of claim 1, wherein the multiple data sources include one of lab results, problem lists, medication lists, radiology reports, pathology reports, operation reports, and admission and discharge notes.

4. The method of claim 1, wherein assigning the relevance score includes applying a weighing factor based on the presence of a second medical code within the one or more medical codes generated by the reasoning outcome.

5. The method of claim 4, wherein the weighing factor is based on a lookup table including relevant combinations of medical codes; and wherein the lookup table has a maximum size of $N^2$, where N is the number of medical codes in the background ontology.

6. The method of claim 1, wherein the one or more medical codes are based on medical ontology comprising Systematic Nomenclature of Medicine and International Classification of Diseases.

7. The method of claim 1, further comprising converting the one or more medical codes generated by the reasoning outcome according to a predetermined medical ontology; and wherein the color coding is based on relevance of the displayed medical code and concept.

8. The method of claim 1, wherein displaying the medical codes in rank order includes displaying a predetermined number of medical codes.

9. The method of claim 1, further comprising receiving a user input based on the displayed list of medical codes.

10. The method of claim 9, wherein the user input selects one of the displayed medical codes to view one of the original data sources for the medical code and the reasoning trail for the medical code.

11. The method of claim 9, wherein the user input filters the displayed medical codes to view medical codes from a selected data source.

12. The method of claim 1, wherein assigning the relevance score to each of the one or more medical codes includes determining a relevance of each of the one or more medical codes relative to a context of a workflow of a user; and wherein the color coding is based on relevance of the displayed medical code.

13. A system, comprising:
a non-transitory computer readable storage medium storing an executable program; and a processor executing the executable program to cause the processor to:

retrieve medical data of a patient, the medical data including data from multiple data sources;

extract ontology and medical concepts from the medical data of the patient including free-text documents by processing natural language;

phenotype, using a machine learning model, the medical data of the patient and the ontology and medical concepts to generate a reasoning trail and reasoning outcome including one or more medical codes and concepts and convert the one or more medical codes and concepts to a predetermined medical ontology, the reasoning trail including a basis for which the reasoning outcome is determined;

when all of the one or more concepts and medical codes are not in the same ontology, map medical codes and concepts onto a medical vocabulary or ontology from one ontology to another;

assign a relevance score to each of the one or more medical codes and concepts;

rank the medical codes and concepts based on the relevance score of each of the one or more medical codes and concepts;

color code at least one of the ranked medical codes or concepts; and display the medical codes and concepts in rank order.

14. The system of claim 13, wherein the processor executes the executable program to cause the processor to:

extract medical concepts from data sources including free-text documents by processing natural language with sentence boundary detection and, wherein phenotyping the medical data includes analyzing the medical concepts.

15. The system of claim 13, wherein the processor executes the executable program to cause the processor to:

filter the ranked medical codes, by selecting only the medical codes having a relevance score above a predetermined threshold value to be displayed.

16. The system of claim 13, wherein assigning the relevance score includes applying a weighing factor based on the presence of a second medical code within the one or more medical codes generated by the reasoning outcome.

17. The system of claim 13, wherein the processor executes the executable program to cause the processor to:

convert the one or more medical codes generated by the reasoning outcome according to a predetermined medical ontology.

18. The system of claim 13, wherein the processor executes the executable program to cause the processor to:

receive a user input based on the displayed list of medical codes.

19. The system of claim 18, wherein the user input one of (a) selects one of the displayed medical codes to view one of the original data sources for the medical code and the reasoning trail for the medical code and (b) filters the displayed medical codes to view medical codes from a selected data source.

20. The system of claim 18, wherein assigning the relevance score to each of the one or more medical codes includes determining a relevance of each of the one or more medical codes relative to a context of a workflow of a user.

21. A non-transitory computer-readable storage medium including a set of instructions executable by a processor, the set of instructions, when executed by the processor, causing the processor to perform operations, comprising:

retrieving medical data of a patient, the medical data including data from multiple data sources;

phenotyping, using a machine learning model, the medical data to generate a reasoning trail and reasoning outcome including one or more medical codes, the reasoning trail including a basis for which the reasoning outcome is determined;

assigning a relevance score to each of the one or more medical codes;

ranking the medical codes based on the relevance score of each of the one or more medical codes;

color coding at least one of the ranked medical codes or concepts; and displaying the medical codes in rank order.

\* \* \* \* \*